US008921475B2

(12) United States Patent
Zech et al.

(10) Patent No.: US 8,921,475 B2
(45) Date of Patent: Dec. 30, 2014

(54) CATIONICALLY HARDENABLE DENTAL COMPOSITION, PROCESS OF PRODUCTION AND USE THEREOF

(75) Inventors: Joachim W. Zech, Kaufering (DE); Thomas Klettke, Diessen (DE); Sebastian Zeller, Cologne (DE); Bernd Kuppermann, Herrsching (DE); Hendrik Grupp, Inning a. Ammersee / Bachern a. Woerthsee (DE)

(73) Assignee: 3M Innovative Properties Company, Saint Paul, MN (US)

( * ) Notice: Subject to any disclaimer, the term of this patent is extended or adjusted under 35 U.S.C. 154(b) by 0 days.

(21) Appl. No.: 13/384,611

(22) PCT Filed: Jul. 19, 2010

(86) PCT No.: PCT/US2010/042405
§ 371 (c)(1),
(2), (4) Date: Jan. 18, 2012

(87) PCT Pub. No.: WO2011/016977
PCT Pub. Date: Feb. 10, 2011

(65) Prior Publication Data
US 2012/0187017 A1 Jul. 26, 2012

(30) Foreign Application Priority Data
Jul. 28, 2009 (EP) .................................... 09166554

(51) Int. Cl.
| | | |
|---|---|---|
| C08K 3/34 | (2006.01) | |
| B22F 1/00 | (2006.01) | |
| C08C 1/06 | (2006.01) | |
| C08K 3/00 | (2006.01) | |
| C08F 2/44 | (2006.01) | |
| C08G 61/02 | (2006.01) | |
| G21F 9/00 | (2006.01) | |
| C08F 2/46 | (2006.01) | |
| A61K 6/10 | (2006.01) | |

(52) U.S. Cl.
CPC ........................................ *A61K 6/10* (2013.01)
USPC ............... 524/493; 524/492; 524/1; 524/498; 524/847; 524/849; 523/1; 588/1; 522/1

(58) Field of Classification Search
CPC ........ C08K 3/36; C08K 3/0033; C08L 83/04; C08F 2/44; A61C 5/00; A61C 13/00; Y10S 75/955; Y10S 260/9981; Y10S 522/908
USPC .......... 524/493, 492, 1, 498, 847, 849; 523/1; 588/1; 522/1
See application file for complete search history.

(56) References Cited

U.S. PATENT DOCUMENTS

| | | | |
|---|---|---|---|
| 3,453,242 A | 7/1969 | Schmitt | |
| 4,167,618 A | 9/1979 | Schmitt et al. | |
| 4,657,959 A | 4/1987 | Bryan et al. | |
| 5,249,862 A | 10/1993 | Herold et al. | |
| 5,286,105 A | 2/1994 | Herold et al. | |
| 5,419,460 A | 5/1995 | Herold et al. | |
| 5,464,131 A | 11/1995 | Keller | |
| 5,569,691 A | 10/1996 | Guggenberger et al. | |
| 5,750,589 A | 5/1998 | Zech et al. | |
| 6,084,004 A * | 7/2000 | Weinmann et al. | 522/25 |
| 6,135,631 A | 10/2000 | Keller | |
| 6,244,740 B1 | 6/2001 | Wagner et al. | |
| 6,395,801 B1 | 5/2002 | Bissinger et al. | |
| 6,599,960 B1 | 7/2003 | Eckhardt et al. | |
| 6,613,437 B1 * | 9/2003 | Eckhardt et al. | 428/413 |
| 2001/0004082 A1 | 6/2001 | Keller et al. | |
| 2003/0153726 A1 | 8/2003 | Eckhardt et al. | |
| 2004/0085854 A1 | 5/2004 | Pauser et al. | |
| 2004/0146713 A1 | 7/2004 | Schaub et al. | |
| 2004/0149164 A1 | 8/2004 | Eckhardt et al. | |
| 2006/0069180 A1 | 3/2006 | Bublewitz et al. | |
| 2008/0200585 A1 * | 8/2008 | Klettke et al. | 523/109 |

FOREIGN PATENT DOCUMENTS

| | | | |
|---|---|---|---|
| EP | 0 231 420 | | 8/1987 |
| EP | 0 232 733 | | 8/1987 |
| EP | 0 863 088 | | 9/1998 |
| WO | WO 01/44873 | | 6/2001 |
| WO | WO 2007/016295 | * | 2/2007 |
| WO | 2007/143490 | * | 12/2007 |
| WO | WO 2007/143490 | | 12/2007 |
| WO | WO 2008/014224 | | 1/2008 |

OTHER PUBLICATIONS

PCT International Search Report from PCT/US2010/042405, dated Jan. 3, 2011, 4 pages.

* cited by examiner

*Primary Examiner* — Ling Choi
*Assistant Examiner* — Jessica E Whiteley
(74) *Attorney, Agent, or Firm* — 3M Innovative Properties Company; Qiang Han

(57) ABSTRACT

The invention relates to a hardenable dental composition comprising component (A) comprising a cationically hardenable compound, component (B) comprising an initiator being able to initiate the hardening reaction of the cationically hardenable compound, and component (C) comprising a filler, wherein the filler comprises a filler body and a filler surface, the filler surface comprising side groups with polar moieties. The invention also relates to a process of producing the dental composition, to the use of the dental composition as dental impression material and to a method of taking an impression of dental tissue.

12 Claims, No Drawings

CATIONICALLY HARDENABLE DENTAL COMPOSITION, PROCESS OF PRODUCTION AND USE THEREOF

CROSS REFERENCE TO RELATED APPLICATIONS

This application is a national stage filing under 35 U.S.C. 371 of PCT/US2010/042405, filed Jul. 19, 2010, which claims priority to European Application No. 09166554.7, filed Jul. 28, 2009, the disclosure of which is incorporated by reference in its/their entirety herein.

FIELD OF THE INVENTION

The invention relates to a hardenable dental composition comprising a cationically hardenable compound, an initiator and a filler, the surface of which comprises reactive moieties. The composition is particularly useful as or for producing dental impression materials and for producing dental crowns and bridges.

BACKGROUND ART

Dental impression materials are used to record the oral situation of a patient. The resulting hardened impression material captures the negative of the oral situation.

Most dental impression materials are delivered in a two or more paste form, containing a base paste and a catalyst paste, which are mixed prior to their application. The mixed pastes are typically applied with the help of a dental tray and/or a syringe-type device. Usually the hardened material can be removed after about one to about six minutes after application. The hardened impression material is used either for making a provisional restoration using a temporary crown and bridge material or for producing a positive model of the oral situation by casting the mould with e.g. gypsum. The obtained positive model is used for making the final restoration in the dental laboratory.

Different types of chemistry can be employed to formulate impression materials. Often used are polyether impression materials which cure by a cationic ring-opening polymerization of aziridines (e.g. Impregum™, 3M ESPE), polysiloxanes which cure via a hydrosilation reaction (e.g. Imprint™, 3M ESPE), polysiloxanes which cure via a condensation mechanism (e.g. Xantropren™, Heraeus Kulzer), mixtures of polyethers and siloxanes which cure via a hydrosilation mechanism (e.g. Senn™, GC) and polyethers which cure via a condensation mechanism (e.g. P2™, Heraeus Kulzer).

To achieve a pasty consistency of the catalyst and the base paste, fillers are typically added. The fillers can also be used to adjust the rheology of the uncured paste.

An improved tensile strength can be desirable to avoid tearing of the set impression material. Tearing of the set impression material may result in loss of information about the clinical situation.

US 2004/0149164 relates to a mixture of elongated N-alkylaziridine prepolymers which can be used as a dental material. The mixture can contain various modifiers like finely divided fillers, pigments, thixotropic agents and surface-active substances.

U.S. Pat. No. 6,599,960 relates to storage-stable cationically polymerzed preparations with improved hardening characteristics. The preparations can contain 0.0005 to 50 wt.-% of soluble and/or fine-particle organic and/or inorganic alkaline earth and/or alkali metal compounds. The preparation can be used for making dental impressions.

U.S. Pat. No. 3,453,242 describes elastomers from polyethers and ethylene imine derivatives. The ethylene imine compouind is subjected to a cross-linking reaction by means of such cross-linking agents as esters of strong acids.

WO 2007/143490 refers to a composition comprising a prepolymer comprising aziridino groups and being characterized by a certain equivalent weight, a crosslinker and an initiators, optionally filler(s) and additive(s). The composition can be used for coating, sealing, moulding, adhering, making impressions and for producing a dental material.

SUMMARY OF THE INVENTION

It would be desirable to increase the amount of filler in order to lower the production costs and/or to improve physical properties like tensile strength.

However, increasing the amount of filler may result in an increase of the overall viscosity and or consistency of the composition. This might be detrimental during a mixing step.

It is an object of the present invention to provide a cationically curable composition having improved properties.

From a clinical standpoint a material can be desirable having an improved viscosity behaviour, especially if the material is applied with a syringe, e.g. around a prepared tooth.

More particularly, it is an object of the present invention to provide a cationically curable dental composition having either improved viscosity behaviour while maintaining the tensile strength or having improved tensile strength while maintaining the viscosity behaviour.

Further, having a storage stable composition can be desirable, too.

In one embodiment, the invention features a hardenable dental composition comprising
  component (A) comprising a cationically hardenable compound,
  component (B) comprising an initiator being able to initiate the hardening reaction of the cationically hardenable and
  component (C) comprising a filler,
wherein the filler comprises a filler body and a filler surface, the surface of the filler comprising side groups with polar moieties.

In another embodiment, the invention features a process of producing such a composition comprising a mixing step.

The invention is also related to a kit of parts and a container containing the components of the inventive composition.

According to a further embodiment, the invention is directed to the use of the dental composition as described in the text of the invention as dental impression material, for producing dental impression materials or for producing crown and bridges Moreover, the invention features a method of taking an impression of dental tissue, comprising the steps of
a) providing a dental composition as described in the text of the invention,
b) placing the dental composition into contact with said dental tissue,
c) allowing the dental composition to harden, and
d) removing the dental composition from the dental tissue.

It has been found that the composition described in the text of the invention fulfils the practitioners' needs especially with regard to viscosity and/or tensile strength properties.

Dental impression materials containing fillers, the surface of which comprises reactive moieties including amino-silane and epoxy-silane moieties, has desirable handling properties (e.g. with respect to rheology) in an uncured state and typically also show improved tensile strength in a cured state.

It was found that by using fillers as described in the text of the invention, compositions can be obtained having a lower viscosity in the uncured state, even if the same amount of filler is used. This indicates that the filler content can even be increased without negatively influencing the desired viscosity value.

Thus, it has been found that a higher amount of filler can be added without jeopardizing the desired rheological properties compared to the state of the art products which typically contain diatomaceous earth.

This can also be beneficial for reducing the production costs, as fillers can often be obtained at a lower price compared to other components (e.g. components with reactive side groups).

It has also been observed that a composition containing the filler as described in the text of the invention has the same consistency as a composition containing filler according to the state of the art.

The inventive compositions typically also have a sufficient shelf life, that is, they can be stored for a sufficient period of time without negatively affecting the desired properties.

With respect to certain compositions (especially those where the surface of the filler used, comprises polar moieties selected from amino-silane moieties, epoxy-silane moieties, or mixtures and combinations thereof) it has also been observed that a possible formation of gas bubbles during production and storage of the respective compositions can be reduced.

DEFINITIONS

Within the description of the invention, the following terms are defined as follows:

The term "compound" is a chemical substance which has a particular molecular identity or is made of a mixture of such substances, e.g., polymeric substances.

By "paste" is meant a soft, viscous mass of solids dispersed in at least one liquid.

A "hardenable compound" within the meaning of the invention is any compound which can be cured or solidified e.g. by chemical crosslinking Chemical crosslinking can be initiated by using a redox or ionic initiator, radiation or heating thereby typically leading to a significant change in rheological properties like viscosity.

An "initiator" within the meaning of the invention is a substance or a group of substances being able to start or initiate the hardening process of a hardenable compound.

The terms "vulcanizing", "hardening", "crosslinking", "curing" and "setting" are used interchangeable and refer to compositions that have as a common attribute the development of a crosslinked polymer from relatively low molecular weight linear or branched polymers or pre-polymers by means of a chemical reaction that simultaneously forms these crosslinks and effectively extends chain length at room temperature.

The term "crosslinked polymer" refers to polymers that are the result of the reaction of the functional group or groups of the polymer chains or prepolymers that were lengthened or connected, e.g., to form a crosslinked network. In contrast to a thermoplastic polymer (i.e., a polymer that softens and flows upon heating) a crosslinked polymer, after crosslinking, is characteristically incapable of further flow.

The term "cationically polymerizable compound" is defined as a compound which can be polymerised using an initiator containing or being able to produce cations.

A "prepolymer" is defined as a compound or a mixture of compounds obtainable by polymerization (such as e.g. polycondensation reaction) of monomers resulting in an intermediate product or mixture of products with increased molecular weight compared to the monomers used. The resulting intermediate product itself bears functional groups (either left over from the initial polymerization or introduced afterwards). The prepolymer containing functional groups can be used for further polymerization reactions (such as e.g. polycondensation reaction or polyaddition reaction) leading to a polymer or polymer mixture or a crosslinked polymer with increased molecular weight compared to the prepolymer.

"Aziridines" are a group of organic compounds sharing the aziridine functional group which is a three membered heterocycle with one amine group and two methylene groups. The parent compound of the aziridines is called aziridine with molecular formula $C_2H_5N$.

An "alkyl-substituted aziridino group" is an aziridine group, wherein at least one of the hydrogen atoms of the methylene groups is substituted by an alkyl group, preferably by a C1 to C4 alkyl group, e.g. methyl, ethyl, n- and iso-propyl or n-, iso- or tert.-butyl group.

In the chemical literature a "methyl substituted aziridine" is sometimes also referred to as "propylene imine".

"Polyether" or "polyether group containing compound" are compounds having a molecular weight of at least about 150 g/mol and containing in the backbone at least about 3, 10 or 20 ether moieties. Polyether containing compositions used as dental impression material can be cured by different mechanisms. Widely used is curing caused by the reaction of aziridine groups with each other.

Examples of polyether groups containing impression materials are given in U.S. Pat. No. 5,569,691, US 2004/0146713 A1 and US 2006/0069180. Commercially available materials are sold e.g. under the brand Impregum™ (3M ESPE).

A "particle" means a substance being a solid having a shape which can be geometrically determined. The shape can be regular or irregular. Particles can typically be analysed with respect to e.g. grain size and grain size distribution. Fillers typically comprise, essentially consist of or consist of particles.

"Room temperature vulcanizing" implies that the curing reaction can proceed at temperatures at or near about 25° C. For example, the oral cavity of the mouth has an average temperature of approximately 32° C. and is therefore near room temperature. Certain "high" temperature cured materials are designed to cure only at relatively high temperatures (e.g., >50° C. or >100° C.) and are stable (i.e., the curing reaction is retarded) at room temperature for prolonged periods. The compositions of the invention are room temperature vulcanizing.

The term "working time" refers to the time between the initiation of the setting reaction (e.g., when a polyether group containing polymer bearing reactive groups and an initiator, being able to start the curing reaction of the polymer are mixed) and the time the setting reaction has proceeded to the point at which it is no longer practical to perform further physical work upon the system, e.g., reform it, for its intended purpose. When the reaction has proceeded to this later point the material is said to have reached its "gel point." The working time preferably provides enough time to mix and place the composition into its desired form. For many dental impression compositions and applications the working time under conditions of use can be greater than about 30 s (seconds), or greater than about 1 min (minute), or greater than about 2 min. Thus, the working time is typically within a range of about 30 s to about 3 min or about 1 min to about 2 min. So-called "fast-setting" compositions typically have a shorter working time, e.g. less than about 2 min or less than about 1.5 min.

The terms "set time" or "setting time" refer to the time at which sufficient curing has occurred so that essentially the material's final cured-state properties are obtained. For a polyether group containing impression material the set time is that time at which one may remove the material from the surface being replicated without causing permanent deformation of the material that would prohibit its use. E.g. for precision impression materials ISO 4823 defines a minimum recovery from deformation of 96.5%. The setting time may be approximated, e.g., by measuring the recovery from deformation after setting at mouth temperature. In general, shorter setting times are preferred over longer setting times. For dental impression compositions the setting time occurs at a time preferably less than about 10 min after initiation of the reaction. More preferably the setting time is less than the sum of about 5 minutes plus the working time.

More specifically, the setting time is the time between positioning of the tray with the dental material in the mouth of the patient and removal of the cured material, and can also be called the mouth residence time or period. Setting times of <about 3 min mouth residence time, preferably <about 2.5 min, and particularly preferably <about 2 min are desirable properties for the dentist working with situation impression materials. For example, the one-phase impression material Imprint™ (3M ESPE) has a setting time of about 5 minutes, while a typical alginate impression material such as Palgat™ (3M ESPE) has a setting time of about 4 min.

By "dental composition" is meant a composition which is intended and adapted to be used in the dental field (including restorative and prosthodontic work) including the orthodontic area. In this respect, a dental composition typically does not contain hazardous substances. Commercially available products have to fulfil requirements such as those given in ISO 4823. Typically, those compositions cure or set at ambient conditions.

A "dental impression" may be described as an accurate representation of part or all of a person's dentition. It forms a "negative" of a person's hard dental tissue which can then be used to make a model (physical) of the dentition. This may be used for the fabrication of dentures, crowns or other prostheses. An impression is typically carried out by placing a viscous material into the mouth in a customised or stock tray. The material then sets to become an elastic solid, and when removed from the mouth retains the shape of the teeth and gingiva. Common materials used for dental impressions include alginate, agar, polyethers including aziridine substituted polyether materials as well as silicones, both condensation-cured silicones and addition-cured silicones including polyvinyl siloxanes.

The term "dental tissue" includes the hard tooth substance (enamel and dentin), the gingival region (soft dental tissue) surrounding the hard tooth substance and hard tooth substance bearing orthodontic appliances.

The term "dental impression materials" comprises precision impression materials, situation impression materials, bite registration materials, duplicating materials (applicable for the duplication of master models, e.g. for all-ceramic restorations requiring a refractory investment model and when inlays, onlays, cantilevers and other precision attachments are being fabricated) and modelling materials (applicable for e.g. reconstructing the gingival, producing crowns and bridges). Duplicating and modelling materials are commercially available e.g. from 3M ESPE AG under the trademarks Reprogum™ or Vestogum™.

The term "automixer-suitable impression material" relates to a multi-component impression material which can be dispensed, for example, from a two-component disposable cartridge through a static mixer, e.g., of SulzerMixpac Company (U.S. Pat. No. 5,464,131, US 2001/0004082) or from tubular film bags in dual-chamber reusable cartridges through a dynamic mixer, e.g., in the "Pentamix™", "Pentamix™ 2" and "Pentamix™ 3" devices of 3M ESPE Company (cf. U.S. Pat. No. 5,286,105 and U.S. Pat. No. 5,249,862).

A "temporary crown and bridge material" within the meaning of the invention is a hardenable material used for making dental crowns and bridges. These materials are typically used during the time period a dental technician needs for producing a permanent prosthetic work such as a crown or bridge. These time periods can last from a few days (1 to about 6 days), a few weeks (1 to about 4 weeks) or a few months (1 to about 6 month).

A "surfactant" is an agent imparting wettability to a material, that is making the material more wettable compared to a material not containing a surfactant. The wettabilty can be determined by the water contact angle which can be measured using e.g. a goniometer DSA 10 (Krüss). A low water contact angle indicates a better wettability.

"Molecular weight" in the context of the invention and if not otherwise indicated always means number average molecular weight ($M_n$).

The molecular weight (Mn) of the polymerizable compound before setting can be determined using nuclear magnetic resonance spectroscopy (end-group determination). In this respect proton ($^1$H) NMR techniques are employed to estimate the molecular weight of the precursor of the prepolymer. Integrated signals of the terminal —CH2- groups are compared to the integrated sum of proton signals from backbone hydrocarbon protons taking into account co-monomer ratio, if applicable. To achieve appropriate separation of terminal methylene proton signals from the backbone proton signals, terminal hydroxyl groups are esterified with trifluoroacetic acid.

"Ambient conditions" within the meaning of the invention mean the conditions which the inventive solution is usually subjected to during storage and handling. Ambient conditions may. for example. be a pressure of about 900 to about 1100 mbar. a temperature of about −10 to about 60° C. and a relative humidity of about 10 to about 100%. In the laboratory ambient conditions are adjusted to about 23° C. and about 1013 mbar.

A composition or solution is "essentially or substantially free of" a certain component within the meaning of the invention, if the composition or solution does not contain said component as an essential feature. Thus, said component is not wilfully added to the composition or solution either as such or in combination with other components or ingredient of other components. A composition being essentially free of a certain component usually contains the component in an amount of less than about 1 wt.-% or less than about 0.1 wt.-% or less than about 0.01 wt.-% with respect to the whole composition. Ideally the composition does not contain the said component at all. However, sometimes the presence of a small amount of the said component is not avoidable e.g. due to impurities.

As used herein, "a", "an", "the", "at least one" and "one or more" are used interchangeably. The terms "comprises" or "contains" and variations thereof do not have a limiting meaning where these terms appear in the description and claims. Also herein, the recitations of numerical ranges by endpoints include all numbers subsumed within that range (e.g., 1 to 5 includes 1, 1.5, 2, 2.75, 3, 3.80, 4.5, etc.).

Unless otherwise indicated, all numbers expressing quantities of ingredients, measurement of properties such as contrast ratio and so forth used in the specification and claims are to be understood as being modified in all instances by the term "about." Accordingly, unless indicated to the contrary, the numerical parameters set forth in the foregoing specification and attached claims are approximations that can vary depending upon the desired properties sought to be obtained by those skilled in the art utilizing the teachings of the present invention. At the very least, and not as an attempt to limit the application of the doctrine of equivalents to the scope of the claims, each numerical parameter should at least be construed in light of the number of reported significant digits and by applying ordinary rounding techniques. Notwithstanding that the numerical ranges and parameters setting forth the broad scope of the invention are approximations, the numerical values set forth in the specific examples are reported as precisely as possible. Any numerical value, however, inherently contains certain errors necessarily resulting from the standard deviations found in their respective testing measurements.

DESCRIPTION OF THE INVENTION

Certain embodiments of the hardenable dental composition can be characterized by at least one or more of the following features:

Consistency (according to ISO 4823): 0, 1, 2 or 3 and/or
Setting time: within about 15 min after mixing at ambient conditions (e.g. 23° C.).

That is, the hardenable dental composition (that is, in its uncured state) can show a comparable low viscous behaviour (consistency 3), a medium to high viscosity (consistency 1 or 2) or show a putty-like behaviour (consistency 0).

Certain embodiments of the hardened dental composition can be characterized by at least one or more of the following features:

Tensile strength (according to DIN 53504): at least about 0.2 MPa, or at least about 1.0,
Elongation at break (according to DIN 53504): at least about 30%, or at least about 50%, or at least about 100%,
Recovery from deformation (according to ISO 4823): at least about 90%, or at least about 95%, or at least about 98%,
Shore A hardness (according to DIN 53505; 24 h): at least about 20 or at least about 30.

If desired, the viscosity can be measured at 23° C. using a Physica/Anton Paar (MCR 300 or MCR 301) device with a plate/plate system (diameter 20 mm) and a slit of 0.2 mm. The viscosity values (Pas) and share stress values (Pa) are recorded for each share rate (.starting from 10 l/s to 100 l/s in 10 l/s and/or 5 l/s steps. For each share rate, a delay of 5 s is used before collecting data. The above mentioned method of measurement corresponds essentially to DIN 53018-1.

If desired, the tensile strength and elongation at break of the compositions can be determined according to DIN 53504. The tensile strength is given in MPa and the elongation in % of the original length. Tensile strength and elongation data are evaluated by tearing six I-shaped specimens with a central unit of 20 mm×4 mm×2 mm in a Zwick Z020 Universal testing machine. Base and catalyst pastes can be mixed through a static mixer (e.g. SulzerMixpac Comp.), by an automatic mixing device (e.g. Pentamix™; 3M ESPE) or by hand and filled into a brass mould. After 24 h at about 23° C. the specimen are removed, six measurements are made and the mean value determined (speed 200 mm/min).

The cationically hardenable compound typically comprises a hardenable prepolymer. The prepolymer comprises typically a backbone and reactive side groups.

The backbone of the prepolymer typically comprises moieties selected from polyether, polyesters, polyurethanes and combinations thereof. From a chemical stability point of view, a polyether moieties containing backbone can be preferred. Those groups typically also improve the hydrophilic properties of the composition.

In certain embodiments the prepolymer does not contain silicone moieties.

According to one embodiment, the inventive dental composition includes a polyether group containing hardenable prepolymer as component (A) or part of component (A), that is, a prepolymer comprising a polyether group and reactive moieties which upon addition of a suitable catalyst or initiator can react with each other and thus form a polymeric network.

The molecular weight (Mn) of the polyether group containing prepolymer is typically in a range from about 150 to about 20,000 g/mol, or in the range from about 250 to about 10,000 g/mol, determined e.g. with GPC methods know to the person skilled in the art.

Suitable polyethers or polyether groups, which can be used, include those which meet the requirements in terms of material properties with regard to the preferred use as dental materials.

Appropriate polyethers or polyether groups can be produced in a manner known to the person skilled in the art by the reaction of the starting compound having a reactive hydrogen atom with alkylene oxides, for example ethylene oxide, propylene oxide, butylene oxide, styrene oxide, tetrahydrofurane or epichlorohydrine or mixtures of two or more thereof.

Especially suitable are polyether compounds which are obtainable by polyaddition of ethylene oxide, 1,2-propylene oxide, 1,2-butylene oxide or tetrahydrofuran or of mixtures of two or more of the mentioned compounds with the aid of a suitable starting compound and a suitable catalyst.

The reaction products of low-molecular-weight polyfunctional alcohols having at least two hydroxyl groups with alkylene oxides, so-called polyethers, may also be used as polyols. The alkylene oxides preferably have from 2 to 4 carbon atoms. Suitable polyols are, for example, the reaction products of ethylene glycol, propylene glycol, butanediol or hexanediol isomers with one or more of the following alkylene oxides: ethylene oxide, propylene oxide or butylene oxides like tetrahydrofurane. Furthermore, the reaction products of polyfunctional alcohols such as glycerol, trimethylolethane or trimethylolpropane, pentaerythritol or sugar alcohols, or mixtures of two or more thereof, with the mentioned alkylene oxides, forming polyether polyols are also suitable. Suitable starting compounds are, for example, water, ethylene glycol, 1,2- or 1,3-propylene glycol, 1,4- or 1,3-butylene glycol, 1,6-hexanediol, 1,8-octanediol, neopentyl glycol, 1,4-hydroxymethylcyclohexane, 2-methyl-1,3-propanediol, glycerol, trimethylolpropane, 1,2,6-hexanetriol, 1,2,4-butanetriol, trimethylolethane, pentaerythritol, mannitol, sorbitol, or mixtures of two or more thereof.

Especially suitable are polyether compounds as are obtainable by polyaddition of ethylene oxide, 1,2-propylene oxide, 1,2-butylene oxide or tetrahydrofuran or of mixtures of two or more of the mentioned compounds with the aid of a suitable starting compound and a suitable catalyst.

For example, polyether polyols which are prepared by copolymerisation of tetrahydrofuran and ethylene oxide in a molar ratio of from 10:1 to 1:1, preferably to 4:1, in the presence of strong acids, for example boron fluoride etherates, are suitable.

It can be preferred, if the curing of the dental composition is effected by compounds comprising aziridino groups, which are sometimes also referred to as ethylene imine groups.

The inventive dental compositions can thus comprise at least a component having on average at least 2 aziridino groups or more and a molecular weight of at least about 500.

The term "on average" is to be interpreted such in the context of the present text that a mixture of a large number of compounds may comprise both compounds having less than 2 aziridino groups and also compounds having more than 2 aziridino groups although, when seen over the entirety of the compounds of component (A), the average functionality of all molecules is, with respect to aziridino groups, 2 or more.

All mentioned types of polyaddition or polycondensation products can be provided with aziridino groups by means of any desired subsequent reactions known to the person skilled in the art. For example, it is possible first to introduce, into an appropriate polymer, substituents which are in turn capable of reacting with suitable aziridine derivatives.

It is also possible to polymerise cyclic ethers, preferably epoxides, onto the chain so that products are obtained which at the end contain substituents which can react with aziridine. There come into consideration, for example, polyethers onto which halo-substituted epoxides, e.g. epibromohydrin, are polymerised.

Suitable possible methods for providing the polymers with aziridino groups are mentioned, e.g., in U.S. Pat. No. 3,453,242.

Suitable polymers can carry the aziridino groups terminally or laterally, or terminally and laterally, but preferably terminally.

The aziridino groups containing polymers typically have a dynamic viscosity η of from 10 to about 500 Pa*s, especially from about 15 to about 300 Pa*s. A preferred viscosity range is from about 20 to about 180 Pa*s at 23° C.

The aziridino equivalent is typically from about 250 to about 25,000 g/equivalent, especially from about 400 to about 10,000 g/equivalent.

A component (A) which can be used may comprise only one type of aziridino group containing polymer. It is, however, likewise possible for a component (A) to comprise two or more different types of aziridino polymers, for example 3, 4 or 5 different types.

A "type of polymer" is understood, in the context of the present invention, to be a polymer as results from the polyaddition or polycondensation of selected monomers under the selected reaction conditions. A type of polymer can accordingly include polymer molecules of differing chemical constitution and differing molecular weight, depending on the reaction conditions selected. However, two reactions carried out using identical monomer compositions under identical reaction conditions always result, in accordance with the invention, in identical types of polymer. Two reactions which are carried out using identical monomers but under different reaction conditions may result in identical types of polymers but need not do so. The crucial factor therein is whether there are identifiable differences—in terms of chemical constitution, molecular weight and further parameters which can be determined—that are of relevance to the material properties. Two reactions which are carried out using different monomer compositions always result, in accordance with the invention, in different types of polymers.

Reactive side groups which pending from or attached to the backbone of the prepolymer include those characterized by the following formula (I)

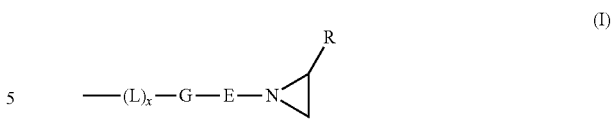

wherein

R represents H, C1-C12 alkyl, C2-C12 alkenyl, C2-C12 alkinyl, C7-C15 alkylaryl, C7-C15 arylalkyl, C3-C12 cycloalkyl, and wherein hydrogen atoms may be replaced by Cl or F and/or wherein up to five carbon atoms may be replaced by atoms or group of atoms selected from O, CO, N, S, E represents a C1-C18 branched or unbranched hydrocarbon chain wherein up to five carbon atoms may be replaced by atoms or group of atoms selected from O, CO, N, S, G represents a group selected from C(O)O, C(O)NR, C(O), C(O)C(O), C(O)(CH2)mC(O) with m=1 to 10, C(S)NR, CH2, L represents O, S, NR with x=0 or 1.

It can be preferred, if the prepolymer has a linear molecular structure. Thus, the prepolymer may typically comprise a linear backbone, which is typically end-capped with cationically hardenable moieties, including aziridino groups. Usually, there are no side chains, especially cationically hardenable side chains pending from the backbone.

Component (A) is typically present in an amount of at least about 5 wt.-% or at least about 12 wt.-% or at least about 20 wt.-%.

Component (A) is typically present up to an amount of about 85 wt.-% or up to about 80 wt.-% or up to about 75 wt.-%.

Typical ranges include from about 5 wt.-% to about 85 wt.-% or from about 12 wt.-% to about 80 wt.-% from about 25 wt.-% to about 70 wt.-%.

Component (A) is typically present in an amount, which allows the formation of a sufficiently crosslinked network, in order to fulfil the practitioners needs.

If the amount of component (A) is too low, the resulting composition might not cure within the desirable period of time or might show not desirable mechanical properties.

The inventive composition also contains an initiator as component (B) or part of component (B) capable of initiating a hardening reaction of component (A).

Depending on the reactive moieties being present in component (A) different initiators have to be used. Useful initiators are typically selected from components, which can be classified as Lewis or Broensted acids. Initiators being able to produce cations, especially H+ has been found to be particularly useful.

If component (A) comprises moieties which can react via a ring-opening reaction, especially via a ring-opening reaction of aziridino groups containing components, the following initiators were found to be useful:

For use in two-component impression materials comprising a curable polyether group containing polymer or derivative described hereinbefore there are suitable those initiator substances which make possible curing of the mixed preparation at room temperature in a period of from about 1 to about 20 minutes to form a resilient solid body, that solid body meeting the requirements for a resilient impression material according to DIN/EN 4823 and having a Shore A hardness (DIN 53 505) of at least 20 after 24 hours.

Sulfonium salts, especially alkyl sulfonium salts or sulfonium salts derived from glutaconic acid were found to be useful. Those and others are described e.g. in US 2008/0200585 A1, U.S. Pat. No. 4,167,618 and US 2003/0153726

A1, the content of which in regard to initiators is explicitly mentioned and herewith incorporated by reference.

Trialkylsulfonium salts as are described in, for example, U.S. Pat. No. 4,167,618 (e.g.: column 2, line 36—column 4, line 32 and Examples) are especially suitable as initiator substances. The mentioned trialkylsulfonium salts are understood as being part of the disclosure of the present text.

In US 2003/0153726 A1, initiators are described which impart just a low degree of acidity to the catalyst component and which make possible a readily adjusted, relatively long processing time after mixing of the basic component and catalyst component has been carried out. Reference is expressly made also to the compounds mentioned therein and the initiator substances mentioned therein are likewise considered part of the disclosure of the present text.

The following initiator compounds were found to be especially useful: zinc salt of p-toluenesulfonic acid, —(S-lauryl-S-ethylsulfonium)butyronitrile tetrafluoroborate, dodecylbenzenesulfonic acid zinc salt, —(S-lauryl-S-ethylsulfonium)-phenylacrylic acid butyl ester tetrafluoroborate.

A further preferred class of initiators can be classified as sulfonium salts or derivatives of glutaconic acid esters as describe in US 2008/0200585 A1. The content of this application with respect to the description of initiators and the way how they can be produced is especially mentioned and herewith incorporated by reference and regarded as part of this invention.

These initiators comprise at least one structural element of the following formula (II)

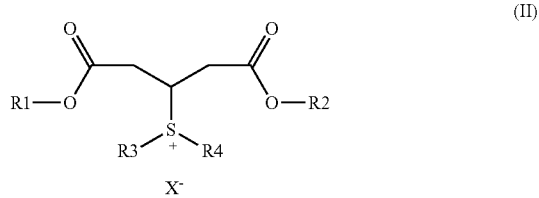

(II)

wherein
X⁻ is a non or low coordinating anion,
R1, R2, R3 and R4 are independently linear, cyclic or branched $C_1$-$C_{20}$ alkyl or alkylene groups, wherein one or more of the methylene groups may be substituted by —CO—, —CONH—, —CON(CH$_3$)—, —S— and/or —O—,
and wherein R1, R2, R3 and/or R4 can act as a bridging element, connecting two or more structural elements.

The term "non or low coordinating group" within the meaning of the invention are anions of strong acids, preferably acids having a pKs value below about 2. Respective examples are $BF_4^-$, $CF_3SO_3^-$, $SbF_6^-$, $AsF_6^-$ or 2,5-di-chlorobenzolsulfonate, but even other low coordinating anions can be used.

The term "bridging element" within the meaning of the invention is defined as a chemical group being able to connect two or more of the aforementioned structural elements comprising at least one sulfonium group. Examples of bridging elements include —(CH$_2$)$_8$—, —(CH$_2$)$_6$— or —(CH$_2$)$_4$— moieties.

It has been observed that a combination of this kind of initiator with the fillers described in the text of this invention, may even further lead to beneficial results, e.g. with respect to tensile strength properties of the cured composition and/or reduction of the formation of gas bubbles during production and/or application of the composition.

The molar ratio between the initiator and the polyether group containing polymer curable by a ring-opening reaction, e.g. a polyether group containing polymer comprising aziridine groups includes ranges from about 1.0:0.1 to about 1.0: 20.0, or from about 1.0:0.5 to about 1.0:10.0, or from about 1.0:0.8 to about 1.0:30.

As the initiator does not only act as a catalyst but chemically react—to a certain extend—with the hardenable composition, a sufficient amount of initiator should be present.

The amount of the component (B) to be used is not particularly limited, unless the desired curing reaction cannot be initiated or catalyzed.

Component (B) is typically present in an amount of at least about 0.1 wt.-% or at least about 0.5 wt.-%.

Component (B) is typically present up to an amount of about 50 or up to about 35 wt.-% or up to about 20 wt.-%.

Typical ranges for the initiator include from about 1 wt.-% to about 50 wt.-% or from about 3 wt.-% to about 40 wt.-% from about 4 wt.-% to about 25 wt.-%, wt.-% with respect to the weight of the whole composition.

If the amount of component (B) is too low, the desired viscosity and/or consistency may not be obtained.

If the amount of component (B) is too high, the resulting composition might not be sufficiently homogenous and the ability to homogenously mix the components (e.g. base and catalyst paste) might be negatively affected.

The inventive dental composition comprises a filler as component (C) or part of component (C). The filler comprises typically a filler body and a filler surface. The filler is typically comprised of particles.

The filler body typically comprises, consists essentially of or consists of $SiO_2$ moieties. Typical examples include quartz, cristobalite and silicates (e.g. components comprising anions of the formula $[SiO_3^{2-}]_n$ or $[Si_2O_5^{2-}]_n$) like wollastonite, nephelinsyenite, kaolin, talcum, feldspar, and mixtures and combinations thereof, wherein quartz and cristobalite are sometimes preferred.

The surface of this filler comprises side groups with polar moieties.

By "side group" it is meant that the polar moiety is not directly attached to the filler body (e.g. like Si—OH moieties being present on the surface of a quartz filler), but that the polar moiety is linked to the surface of the filler body by a spacer group.

"Polar moieties" are defined as chemical groups having a dipole moment. Examples of such chemical groups include ethers, alcohols, thioles, phosphines, amines (prim., sec., tert.), amide, urethanes, esters, oxiranes, oxetanes, hydrated furanes, thiiranes and combinations thereof.

Side groups with polar moieties can be attached to the filler surface by applying the following steps: dispersing the filler in a solvent, adjustment of the pH, adding of a silane coupling agent, heat treatment, removal of solvent, drying of the filler, solvent exchange process, milling of the filler.

Silane coupling agents, which can be used for the surface-treatment of the filler include substances which can be characterized by formula (III):

E-F-G (III)

wherein E comprises a polar moiety (as described above), F comprises Si, and G comprises at least one hydrolysable group.

By "hydrolysable group" is meant a group, which can react e.g. with OH-groups being present on the surface of the filler.

Examples of hydrolysable groups include halogens (e.g. F, Cl and Br), pseudo-halogens (e.g. azides) and alcoholates (e.g. C1-C6, alkyl and aryl).

More specifically, silane coupling agent which can be used include those which can be characterized by formula (IV)

$$A_m\text{-}B\text{-}Si(R^1)_n(OR^2)_{3-n} \qquad (IV)$$

with A comprising a polar moiety (including —O—, —S—, —NH—, —OH, —SH, —CO—, —CO—O—, —CO—NH— and combinations thereof, wherein moieties comprising amines, oxiranes, and combinations thereof are preferred, B comprising a spacer group, such as (i) linear or branched C1 to C12 alkyl, (ii) C6 to C12 aryl, (iii) organic group having 2 to 20 carbon atoms bonded to one another by one or more ether, thioether, ester, thioester, thiocarbonyl, amide, urethane, carbonyl and/or sulfonyl linkages,
$R^1$ comprising an alkyl group (e.g. C1 to C6) or an aryl group (e.g. C6 to C12), and
$R^2$ comprising an alkyl group (e.g. C1 to C6),
with m=1, 2, 3 or 4 and n=0, 1 or 2.

Non-polar moieties are e.g. —Si—OR, —Si—O—Si—, —Si—R, with R being alkyl (e.g. C1 to C6) or aryl (e.g. C1 to C6). These kinds of moieties do not show a sufficient dipole moment.

Preferably, the surface of the filler should not contain or be essentially free of acidic groups like —COOH and —SO₃H.

The pH value of a 10 wt.-% dispersion of the filler in water is typically within the range from about 7 to about 12. Using a filler having a pH value within this range can be beneficial to improve the storage stability and shelf life of the composition.

The pH value can be determined with means known to the person skilled in the art.

The BET surface of the filler is typically in a range from about 0.05 to about 50 m²/g or from about 0.5 to about 30 m²/g or from about 0.5 to about 20 m²/g. Using a filler with a BET surface within this range can be beneficial to adjust the viscosity and tensile strength.

If desired, the BET surface of the filler can be determined as described in DIN 66132. Alternatively, the values for the BET surface are taken from a material data sheet provided by the supplier.

The following commercially available fillers were found to be particularly useful: quartz comprising amino-silane groups (e.g. Silbond™ 600 AST, Silbond™ 800 AST; Quarzwerke Frechen), wollastonite comprising amino-silane groups (e.g. Tremin™ 283-600 AST or Tremin™ 939-300 AST; Quarzwerke Frechen), quartz/kaolin mixture comprising amino-silane groups (e.g. Aktisil™ AM; Quarzwerke Frechen), quartz comprising epoxy groups (e.g. Silbond™ 600 EST, Silbond™ 800 EST; Quarzwerke Frechen), cristobalite comprising amino-silane groups (e.g. Silbond™ 6000 AST, Silbond™ 8000 AST) and cristobalite comprising epoxy groups (e.g. Silbond™ 6000 EST, Silbond™ 8000 EST).

The size of the filler particles should be such that a homogeneous mixture can be obtained. The particle distribution is preferably chosen such that there are no fillers with particle sizes of more than 50 µm.

Typically, the size of the filler particles (d50 value) is below about 40 µm or below about 10 µm or below about 5 µm. Typical ranges (d50 value) include from about 0.1 to about 40 µm or from about 0.5 to about 20 µm or from about 1 to about 10 µm.

If the filler particles are too small, the viscosity of the resulting composition might increase to a not desirable limit.

If the filler particles are too big, the detail accuracy might be negatively affected.

It can be advantageous if the pH value of a dispersion of the filler in water is above about 7 or above about 8. Useful ranges include from about 7 to about 12 or from about 8 to about 11 or from about 7 to about 10.

If desired, the pH value of the filler can be determined as follows: 20 g of filler are put into a cup, combined with 50 ml of a calcium chloride solution (0.01N) and 4 ml ethanol. The suspension is stirred for 10 min. After 1 h the pH value of the suspension is determined using a calibrated pH electrode while stirring (e.g. Titrando™ Profitrode™)

It was found that by using a filler having a pH value above the values or within this ranges described above might be beneficial for enhance the storage stability.

The filler can be present in an amount of at least about 1 wt.-% or at least about 5 wt.-% or at least about 10 wt.-% with respect to the whole composition.

There is no particular upper limit, however, typically the amount of filler, if present at all, is used in an amount of at most about 80 wt.-% or at most about 75 wt.-% or at most about 70 wt.-% with respect to the whole composition.

Thus, typical ranges for the filler as component (C) include from about 10 to about 80 or from about 15 to about 75 or from about 20 to about 70 wt.-% with respect to the whole composition.

If the amount of component (C) is too low, the desired tensile strength might not be obtained.

If the amount of component (C) is too high, the elasticity of the cured composition might negatively be affected and the viscosity of the un-cured composition might be too high. Moreover, the shelf life might negatively be influenced.

Besides the filler described above as component (C), which is present in the hardenable dental composition of the present invention, the hardenable dental composition can also comprise other filler(s) in addition.

E.g., besides certain surface-treated fillers, non-surface treated fillers can be added. A "non-surface treated filler" in the context of the invention is a filler having a surface which has not been exposed to reactive substances resulting in a modification of the surface of the filler to make the filler more compatible with other components of the composition.

A wide variety of inorganic, hydrophilic or hydrophobic fillers may be employed such as silicas, aluminas, magnesias, titanias, inorganic salts, metallic oxides, quartz, cristobalit, kaolin, talcum, feldspar, wollastonit, nephelinsyenit, silicates and glasses. It has been found to be possible to employ mixtures of silicone dioxides, such as a diatomaceous earth and/or fumed silica. Those filler are commercially available from companies like Cabot Corporation, Wacker or Degussa under the trade names Aerosil™ (Degussa) HDK-H (Wacker), Cab-o-Sil (Cabot).

More specifically, fillers which can be used include calcium silicate, diatomaceous earth, zirconium silicate, montmorillonite such as bentonite, zeolite, including molecular sieves such as sodium aluminium silicate, barium sulphate, calcium carbonate, plaster, glass and plastic powder.

The sizes and surface areas of the foregoing materials can be adjusted to control the viscosity and thixotropicity of the resulting compositions. The particle distribution is preferably chosen such that there are no fillers with particle sizes of more than about 50 µm.

If a further filler component is present, this filler component can be designated as component (C2), whereas the filler component, the surface of which comprises polar moieties can be designated as component C1).

A combination of reinforcing and non-reinforcing fillers can be preferred.

The quantity of reinforcing fillers can range from about 0 to about 10 wt.-%, in particular from about 0.2 to about 7 wt.-% with respect to the whole composition.

Typical reinforcing fillers include fumed silica, carbon black and the like. They also can improve mechanical properties like tensile strength or tear strength, of the cured silicone composition.

Typical non-reinforcing fillers include precipitated silicas, diatomaceous earth, aluminas, magnesias, titanium dioxide, zirconium silicate and mixtures and combinations thereof.

A combination of reinforcing and non-reinforcing fillers sometimes even further improves the rheology of the uncured composition and the elasticity of the cured composition.

According to a further embodiment, the composition can also comprise a component (D) comprising one or more additives.

Additives include retarders to modify the working and setting time, rheology modifier(s), thixotropic agent(s), diluting agent(s), inhibitor(s), pigment(s), dye(s), plastizer(s), odorous substance(s), flavouring(s), stabilizer(s), alone in admixture or combination.

All kinds of known and compatible softeners and rheology modifiers like non reactive polymeric fluids or fats commonly used in commercialized impression materials can be added as well as pigments and stabilizers of any kind.

Preferred are those ingredients and additives that do not add unpleasant smell or taste. Compounds that have an unpleasant smell might be removed by thinfilm evaporation, if needed.

Typical plasticisers include, e.g., compounds of the ester type such as C12- to C15-alkyl lactates, ethyl or butyl esters of citric acid or of acetylcitric acid, phthalic acid esters of relatively long, branched alcohols such as bis(2-ethylhexyl) phthalate or phthalic acid polyester, C2- to C22-dialkyl esters of C2- to C6-dicarboxylic acids such as bis(2-ethylhexyl) adipate, dioctyl maleate, diisopropyl adipate, aromatic and aliphatic sulfonic acid esters such as C2- to C20-alkylsulfonic acid esters of phenol or of C1- to C22-alkanols or typical aromatic plasticisers such as polyphenyls in a wide viscosity range, including wax-like polyphenyls such as are obtainable, for example, from the Monsanto company, isomeric mixtures of C20 to C40 aromatic compounds, with preference being given to the use of mixtures of plasticisers of the ester type and aromatic type.

Liquids such as C12-C15 alkyl acetates, liquid derivatives of citric acid, esters of phthalic acid with branched alcohols like bis(2-ethylhexyl)phthalate or polymeric phthalates, C2-C18 bis(alkyl)esters of C2-C6 dicarboxylic acids like dioctylmaleate, dioctyladipate, aromatic and aliphatic esters of sulfonic acids like Mesamoll™, aromatic and aliphatic amides of sulfonic acides like N-ethyl toluene solfonic acid amide or N-butyl benzene solfonic acid amide, typical aromatic diluters like poly phenyls, xylyl toluene, and dixylyl toluene can be used. Also low molecular weight alcohols that may contain more than one OH-function like propane-1,2-diol may be used. From the group of polymeric compounds, polypropylene glycols and its derivatives are sometimes preferred.

Suitable diluting agent(s) usually do not contain reactive moieties like —SH or —COOH, primary or secondary amino groups, but may contain —OH. Liquids such as $C_{12}$-$C_{15}$ alkyl acetates, liquid derivatives of citric acid, esters of phthalic acid with branched alcohols like bis(2-ethylhexyl)phthalate or polymeric phthalates, $C_2$-$C_{18}$ bis(alkyl)esters of $C_2$-$C_6$ dicarboxylic acids like dioctylmaleate, dioctyladipate, aromatic and aliphatic esters of sulfonic acids like Mesamoll™, aromatic and aliphatic amides of sulfonic acides like N-ethyl toluene solfonic acid amide or N-butyl benzene solfonic acid amide, typical aromatic diluters like poly phenyls, dibenzyl toluene, xylyl toluene, dixylyl toluene and polymeric compounds like polyethers, polyesters, polycarbonates, polyolefines can be used. Also low molecular weight alcohols that may contain more than one OH-function like propane-1,2, diol may be used. From the group of polymeric compounds, polypropylene glycols and its derivatives are preferred.

The composition typically does not contain water, especially added water. However, small amounts of water (e.g. below about 3 wt.-% or below about 1 wt.-%) might be present due to the natural water content of the individual components of the formulation.

An example of a preferred plasticiser combination is a mixture of acetyl tributyl citrate and dibenzyltoluene.

Likewise suitable as additives are triacyl esters of glycerol of non-animal origin. Suitable additives can consist of, for example, modified fats of vegetable origin such as hydrogenated palm oil or soybean oil or synthetic fats.

Suitable fats are described in U.S. Pat. No. 6,395,801, to the full content of which reference is here made. Avocado oil, cottonseed oil, groundnut oil, cocoa butter, pumpkin seed oil, linseed oil, maize germ oil, olive oil, palm oil, rice oil, rapeseed oils, safflower oil, sesame oil, soybean oil, sunflower oil, grapeseed oil, wheat germ oil, Borneo tallow, fulwa butter, hemp oil, illipé butter, lupin oils, candlenut oil, kapok oil, katiau fat, kenaf seed oil, kekuna oil, poppy seed oil, mowrah butter, okra oil, perilla oil, sal butter, shea butter and tung oil are especially suitable, provided that the fats in question have been hydrogenated before use. Suitable hydrogenated fats are considered to be those whose iodine value is less than 20 (measured in accordance with the DGF [German Society for Fat Science] standard C-V 11 Z2). Fat hydrogenation procedures are described, for example, in "Ullmanns Enzyklopädie der industriellen Chemie", 4th edition, volume 11, p. 469.

Mixtures of naturally occurring fats, and also synthetically prepared fats such as Softisan™ 154 or Dynasan™ 118 (from Hüls Comp.) can likewise be used. The preparation of such synthetic triacyl glycerides is relatively simple for the person skilled in the art and can be carried out by starting from glycerol and the appropriate fatty acid methyl esters. Such esterification reactions are described in, inter alia, "Houben-Weyl, Methoden der Organischen Chemie", Vol. E5/Part 1, p. 659 ff.

Preferred triacyl glycerides correspond to the formula (V):

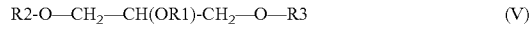

$$R2-O-CH_2-CH(OR1)-CH_2-O-R3 \quad (V)$$

in which R1, R2 and R3 denote, each independently of the others, $C_{11}H_{23}CO$, $C_{13}H_{27}CO$, $C_{15}H_{31}CO$ or $C_{17}H_{35}CO$. Mixtures of such triacyl glycerides can also be used.

Suitable thixotropic agent(s) which can be added to the composition of the invention are organic compounds e.g. waxes according to the definition in Ullmanns Enzyklopädie der technischen Chemie, 4. Auflage, Verlag Chemie, Weinheim, Band 24, page 3 or triglycerides as described in U.S. Pat. No. 6,127,449. In general all organic non-water based thixotropic agents are suitable. That means that suitable thixotropic agents can alter the rheology especially of non-water based formulation.

There is no need for additive(s) (D) to be present, however, if additive(s) (D) are present, they are typically present in an amount of at least about 0 wt.-% or at least about 0.005 wt.-% or at least about 0.01 wt.-%.

Component (D) can be present up to an amount of about 50 wt.-% or up to about 40wt.-% or up to about 35 wt.-%.

Typical ranges include from about 0 wt.-% to about 50 wt.-% or from about 0.005 wt.-% to about 40 wt.-% from about 0.01 wt.-% to about 35 wt.-%.

If additive(s) are present they are typically present in an amount sufficient and not detrimental to the desired effect or effects to be achieved.

The curable dental composition of the invention may also include a component (E) comprising one or more surfactant, especially a Si-containing surfactant or mixture of Si-containing surfactants. Hereinafter, Si-containing surfactants are referred to as component (E1). If desired, two or more surfactancts can be present referred to as component (E1), (E2) etc.

There is no need for component (E1) to be present, however, if component (E1) is present, it is typically present in an amount of at least about 0 wt.-% or at least about 0.1 wt.-% or at least about 0.5 wt.-%.

Component (E1) can be present up to an amount of about 5 wt.-% or up to about 6 wt.-% or up to about 7 wt.-%.

Typical ranges include from about 0 wt.-% to about 7 wt.-% or from about 0.1 wt.-% to about 6 wt.-% from about 0.5 wt.-% to about 5 wt.-%.

If component (E1) is present it is typically present in an amount sufficient and not detrimental to the desired effect or effects to be achieved (e.g. improving the de-gassing behaviour and/or the hydrophilicity of the curable composition).

Surfactants or hydrophilizing agents which can be employed can generally be chosen freely from all types of surfactants which improve the hydrophilicity of a polyether group containing polymer.

Preferably, the use of the surfactant should not negatively impact the material properties or curing behavior of the curable composition or at least not more than avoidable or tolerable.

Component (E1) can comprise an agent or a plurality of agents which are generally capable of increasing the hydrophilic character to a composition, for example as demonstrated by a decrease in the wetting angle of a drop of water or an aqueous solution or dispersion (e.g. a plaster suspension or the like) on the material (in its cured or uncured state) over that wetting angle achieved on the same composition without component (E1).

In certain embodiments, the surfactant does not contain reactive groups so that it is not incorporated into the network of the hardenable composition.

Useful surfactants also include polyether carbosilanes of the general formula (VI)

Q-P—(OC$_n$H$_{2n}$)$_x$—OZ  (VI)

in which Q stands for R$_3$Si— or R$_3$Si—(R'—SiR$_2$)$_a$—R'—SiR"$_2$—, where every R in the molecule can be the same or different and stands for an aliphatic C1-C18, a cycloaliphatic C6-C12 or an aromatic C6-C12 hydrocarbon radical, which can optionally be substituted by halogen atoms, R' is a C1-C14 alkylene group, R" is R in the case of a≠0 or is R or R$_3$SiR' in the case of a=0, and a=0-2; P stands for a C2-C18 alkylene group, preferably a C2-C14 alkylene group or A-R''', where A represents a C2-C18 alkylene group and R''' a functional group selected from: —NHC(O)—, —NHC(O)—(CH$_2$)$_{n-1}$—, —NHC(O)C(O)—, —NHC(O)(CH$_2$)$_v$C(O)—, —OC(O)—, —OC(O)—(CH$_2$)$_{n-1}$—, —OC(O)C(O)—, —OC(O)(CH$_2$)$_v$C(O)—, —OCH$_2$CH(OH)CH$_2$OC(O)(CH$_2$)$_{n-1}$—, —OCH$_2$CH(OH)CH$_2$OC(O)(CH$_2$)$_v$C(O)— with v=1-12; Z is H or stands for a C1-C4 alkyl radical or a C1-C4 acyl radical; x stands for a number from 1 to 200 and n stands for an average number from 1 to 6, preferably 1 to 4. Thus, the element —SiR'$_2$— can also comprise the substructure —Si(R)(R$_3$SiR')—.

The polyether part can be a homopolymer, but can also be a statistical, alternating or block copolymer.

Also possible is the use of polyether carbosilanes selected from the group consisting of:
Et$_3$Si—(CH$_2$)$_3$—O—(C$_2$H$_4$O)y-CH$_3$, Et=Ethyl
Et$_3$Si—CH$_2$—CH$_2$—O—(C$_2$H$_4$O)y-CH$_3$, Et=Ethyl
(Me$_3$Si—CH$_2$)$_3$Si—(CH$_2$)$_3$—O—(C$_2$H$_4$O)y-CH$_3$, Me=Methyl
Me$_3$Si—CH$_2$—SiMe$_2$-(CH$_2$)$_3$—O—(C$_2$H$_4$O)y-CH$_3$, Me=Methyl
(Me$_3$Si—CH$_2$)$_2$SiMe—(CH$_2$)$_3$—O—(C$_2$H$_4$O)y-CH$_3$, Me=Methyl
Me$_3$Si—(CH$_2$)$_3$—O—(C$_2$H$_4$O)y-CH$_3$, Me=Methyl
Me$_3$Si—CH$_2$—CH$_2$—O—(C$_2$H$_4$O)y-CH$_3$, Me=Methyl
Ph$_3$Si—(CH$_2$)$_3$—O—(C$_2$H$_4$O)y-CH$_3$, Ph=phenyl
Ph$_3$Si—CH$_2$—CH$_2$—O—(C$_2$H$_4$O)y-CH$_3$, Ph=phenyl
Cy$_3$Si—(CH$_2$)$_3$—O—(C$_2$H$_4$O)y-CH$_3$, Cy=cyclohexyl
Cy$_3$Si—CH$_2$—CH$_2$—O—(C$_2$H$_4$O)y-CH$_3$, Cy=cyclohexyl
(C$_6$H$_{13}$)$_3$Si—(CH$_2$)$_3$—O—(C$_2$H$_4$O)y-CH$_3$
(C$_6$H$_{13}$)$_3$Si—CH$_2$—CH$_2$—O—(C$_4$H$_4$O)y-CH$_3$ in which y conforms to the relation: 5≤y≤20.

Surfactants which can also be used, either alone or as a mixture of two or more thereof, can be found in U.S. Pat. No. 5,750,589 (Zech et al), col. 2, l. 47 to col. 3 l. 27 and col. 3, l. 49 to col. 4, l. 4 and col. 5, l. 7 to col. 14, l. 20.

Other surfactants which can be used, either alone or as a mixture of two or more thereof, can be found in U.S. Pat. No. 4,657,959 (Bryan et al.), col. 4, l. 46 to col. 6. l. 52 as well as in EP 0 231 420 B1 (Gribi et al.; also published as AU 6,857,087) p 4, l. 1 to p. 5, l. 16 and in the examples.

U.S. Pat. No. 5,750,589, U.S. Pat. No. 4,657,959 and EP 0 231 420 B1 are expressly described and cited herein as a source of disclosure for compounds which can be used as component (E1) according to the invention.

Some of the surfactants, which can be used as component (E1) or part of component (E1) can be summarized under the following formula (VII)

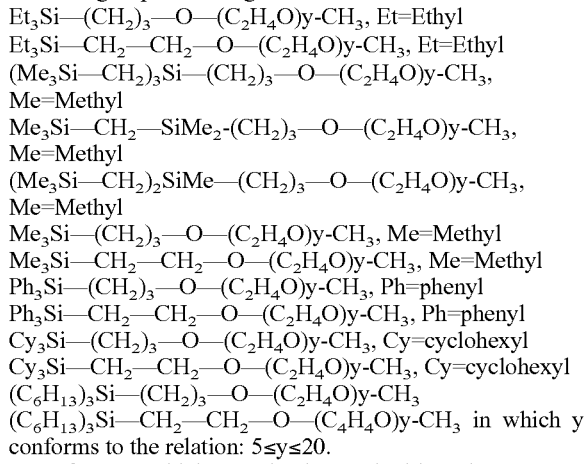

(VII)

where each R is independently a monovalent hydrocarbyl radical with 1 to 22 C-atoms, R$^1$ is a divalent hydrocarbylene radical 1 to 26 C-atoms, each R$^2$ is independently hydrogen or a lower hydroxyalkyl radical, R$^3$ is hydrogen or a monovalent hydrocarbyl radical with 1 to 22 C-atoms, n and b are independently greater than or equal to zero, and m and a are independently greater than or equal to one, with the proviso that a has a sufficient value and b is small enough so that a cured composition of the invention has the desired water contact angle.

Preferably R and R$^3$ are —CH$_3$, R$^1$ is —C$_3$H$_6$—, R$^2$ is hydrogen, n is about zero or about one, m is about one to about five, a is about five to about 20 and b is about 0.

Several of such ethoxylated surfactants are for example available from Momentive Performance Materials Inc. including "SILWET™" surface active copolymers. Preferred surface active copolymers include Silwet 35, Silwet L-77, Silwet L-7600 and Silwet L-7602, Silwet L-7608 and Silwet Hydrostable 68 and Silwet Hydrostable 611. Silwet L-77 is an especially preferred ethoxylated surfactant which is believed to correspond to the above formula where R and $R^3$ are —$CH_3$, $R^1$ is —$C_3H_6$—, $R^2$ is hydrogen, n is about zero or about one, m is about one or about two, a is about seven, and b is about 0. Also possible is the use of MASIL™ SF19, as obtainable from Lubrizol performance products, Spartanburg, US.

The curable dental composition of the invention may also comprise a component (E2) comprising a hydrocarbon surfactant or mixture of surfactants.

The inventive composition is typically obtained by mixing a base paste and a catalyst paste. In this respect, the surfactant can be present in the base paste or the catalyst paste, or in the base paste and the catalyst paste. In one embodiment of the invention, the surfactant is present in the base paste only.

There is no need for component (E2) to be present, however, if component (E2) is present, it is typically present in an amount of at least about 0 wt.-% or at least about 0.01 wt.-% or at least about 0.1 wt.-%.

Component (E2) can be present up to an amount of about 10 wt.-% or up to about 15 wt.-% or up to about 20 wt.-%.

Typical ranges include from about 0 wt.-% to about 20 wt.-% or from about 0.01 wt.-% to about 15 wt.-% from about 0.1 wt.-% to about 10 wt.-%.

If component (E2) is present it is typically present in an amount sufficient and not detrimental to the desired effect or effects to be achieved (e.g. improving the de-gassing behaviour and/or the hydrophilicity of the curable composition).

Useful surfactants, which can improve the hydrophilicity of a polyether group containing polymer according to the invention, can generally be chosen from anionic, cationic or non-ionic surfactants or mixtures of two or more of such types of surfactants.

Examples of useful non-ionic surfactants include those according to the formula (VIII):

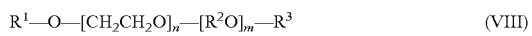

$$R^1-O-[CH_2CH_2O]_n-[R^2O]_m-R^3 \qquad (VIII)$$

wherein $R^1$ represents hydrogen or an aromatic or aliphatic, linear or branched hydrocarbon group having 1-20 carbon atoms, $R^2$ represents an alkylene having 3 carbon atoms, $R^3$ represents hydrogen or a C1-C3 alkyl group, n has a value of 0 to 40, m has a value of 0 to 40 and the sum of n+m being at least 2.

It will be understood that in the above formula, the units indexed by n and m may appear as blocks or they may be present in an alternating or random configuration. Examples of non-ionic surfactants according to the formula above include alkylphenol oxethylates such as ethoxylated p-isooctylphenol commercially available under the brand name TRITON™ such as for example TRITON™ X 100 wherein the number of ethoxy units is about 10 or TRITON™ X 114 wherein the number of ethoxy units is about 7 to 8.

Still further examples include those in which $R^1$ in the above formula represents an alkyl group of 4 to 20 carbon atoms, m is 0 and $R^3$ is hydrogen. An example thereof includes isotridecanol ethoxylated with about 8 ethoxy groups and which is commercially available as GENAPOL™X080 from Clariant GmbH.

Non-ionic surfactants according to the above formula with $R^1$ and $R^3$ representing a C1-C3 alkyl chain or hydrogen and in which the hydrophilic part comprises a block-copolymer of ethoxy groups and propoxy groups may be used as well. Such non-ionic surfactants are commercially available from Clariant GmbH under the trade designation GENAPOL™ PF 40 and GENAPOL™ PF 80. Further suitable non-ionic surfactants that are commercially available include Tergitol™ TMN 6, Tergitol™ TMN 10, or Tergitol™ TMN 100X. Also statistical, alternating or block copolymers of ethylene oxide and propylene oxide are suitable surfactants according to the present invention. Such non-ionic surfactants are available e.g. under the trade name Breox™ A, Synperonic™ or Pluronic™.

In a particular embodiment of the present invention, a mixture of a Si-containing surfactant, for example a Si-surfactant as exemplified above as component (E1), and one or more non-ionic surfactants selected from hydrocarbon surfactants as described above as component (E2) can be used.

This combination was found to be particular useful not only to improve the de-gassing behaviour but also to improve the hydrophilicity of the curable dental composition.

The inventive composition may also comprise in addition to other ingredients and surfactants, alone or in combination an F-containing component including those described in EP application number 09162681.2, especially those described on pages 21 to 27.

According to one embodiment of the invention, the composition can comprise the individual components in the following amounts:

Component (A): from about 5 wt.-% to about 85 wt.-% from about 12 wt.-% to about 75 wt.-% from about 45 wt.-% to about 60 wt.-%, Component (B): from about 1 wt.-% to about 50 wt.-% or from about 3 wt.-% to about 40 wt.-%, Component (C): from about 10 wt.-% to about 80 wt.-% or from about 15 wt.-% to about 75 wt.-%, Component (D): from about 0 wt.-% to about 50 wt.-% or from about 0.2 wt.-% to about 40 wt.-% or from about 0.5 wt.-% to about 30 wt.-%, Component (E1): from about 0 wt.-% to about 7 wt.-% or from about 0.1 wt.-% to about 6 wt.-% or from about 0.5 wt.-% to about 5 wt.-%, Component (E2): from about 0 wt.-% to about 15 wt.-% or from about 0.1 wt.-% to about 8 wt.-% or from about 0.5 wt.-% to about 5 wt.-%, wt.-% with respect to the whole composition.

The mixture to be used in the process of the present invention does typically not contain components which are not desirable form a toxicological standpoint of view and may easily leak from or migrate out of the mixed composition, especially when the composition is placed into a patients' mouth.

The invention is also directed to a process of production or manufacturing the dental composition. Such a process comprises at least one mixing or compounding step of the individual component of the composition. Mixing or compounding can be accomplished by using a kneader or a dissolver. Typically, the fillers are added to the other components. This typically facilitates the mixing procedure.

The dental composition according to the invention is typically provided in separate parts and comprises at least a curable base paste and a catalyst or initiator paste comprising a catalyst or initiator suitable for curing at least part of the material of the base paste.

Accordingly, the components of the composition can be included in a kit, where the contents of the composition are packaged to allow for storage of the components until they are needed. When used, the components of the compositions can be mixed in the suitable amounts and clinically applied using conventional techniques.

Thus, the invention also relates to a kit of parts, comprising a base paste and a catalyst paste separated from each other before use, wherein the base paste comprises component (A)

and the catalyst paste comprises component (B) and wherein components (C), and optional component(s) (D), (E1), and (E2) is/are present either in the base paste or the catalyst paste or in the base paste and the catalyst paste.

It can be preferred, if the filler (component (C)) is present in the base paste only. This may be desirable from a chemical stability point of view. If the filler is present in the base paste only, the shelf life might be improved.

If the filler is present in the base paste, it is typically present in an amount of at least about 1 or at least about 5 or at least about 10 wt.-%, wt.-% with respect to the weight of the base paste. Typical ranges include from about 5 to about 70 or from about 10 to about 50 or from about 15 to about 45, with respect to the weight of the base paste.

The more equal the viscosity of the base paste compared to the catalyst paste is, and the lower the overall viscosity is, the easier the mixing can typically be achieved, especially if the mixing is done using a static mixing tip.

The volume ratios of catalyst paste and base paste can range from about 10:1 to about 1:10. Particularly preferred volume ratios of base paste to catalyst paste are from about 1:1 to about 10:1 or from about 2:1 to about 5:1 (e.g. 5 parts of base paste to 1 part of catalyst paste).

Generally, mixing and dosing of the components can be performed manually, e.g., by spatula (strand-length comparison) or a manually operated pre-filled dual cartridge dispenser with static mixing tips, or automated, using one of the various available devices available for such an automated task, preferably one of the devices mentioned in EP 0 232 733 A1, U.S. Pat. No. 6,135,631 or EP 0 863 088 A1 together with a dynamic mixing tip as mentioned in US 2004/0085854 or U.S. Pat. No. 6,244,740.

A further improvement of the handling properties of dental compositions can be seen in using an automatic mixing and metering systems for two-component compositions which have automatic conveying and mixing units, such as are described e.g. in U.S. Pat. No. 5,249,862, U.S. Pat. No. 5,286, 105 and U.S. Pat. No. 5,419,460. The need for manual mixing of base pastes and catalyst pastes, above all when mixing larger quantities of material, can be eliminated, since this can take place automatically and within a short period of time. The result is usually a homogeneous product which is essentially free of air bubbles. Commercially available devices are distributed by 3M ESPE under the brand Pentamix™ or Pentamix™ 2 or Pentamix™ 3.

In practice, the impression material can be syringed through a static or mechanical mixing device into an impression tray or onto the patients' teeth or tissue and placed in the patients' mouth. The mixed pastes may also be applied using an applicator like an elastomer syringe. After the impression material is set, the tray is removed from the patient's mouth and, in instances where the dental practitioner prepares the positive model, it may be preferable to pour the positive model material immediately after removal of the impression from the patient's mouth.

If used in the dental field, the composition can be applied using e.g. the following steps:
  providing the composition as described in the text of the invention,
  applying the composition to a surface,
  letting the composition set.

The surface can be the surface of soft or hard oral tissue, the surface of an impression material, preferably of a cured impression material, the surface of a crown or the surface of a model of a tooth stump.

The inventive dental composition can be used broadly for coating substrates, as sealing material, moulding material, for adhesively fixing substrates and/or making impressions, for modeling of objects or body parts.

In particular, the invention is also directed to a method of taking an impression of a dental tissue, comprising the steps:
e) providing a dental composition as described in the text of the invention
f) placing the dental composition into contact with said dental tissue,
g) allowing the dental composition to harden, and
h) removing the dental composition from the dental tissue.

The dental material or composition can be used as impression material or for the production of crowns and/or bridges, including temporary or long term crowns and bridges. In the latter case, the composition is used as a mould to be filled with the (temporary or long term) crown and/or bridge material, which is typically based on polymerizable(meth)acrylates or similar chemical reactants.

The curable composition is especially useful for producing dental materials like precision impression materials, bite registration materials, duplicating materials, modelling materials, situation impression materials.

The composition can be used e.g. for making impressions of soft and hard dental tissue. This can be achieved simply, e.g. filling the material into a dental tray and putting the tray into the mouth of a patient.

If used in the dental field, curing is preferably carried out at a temperature below about 50° C. and preferably below about 40° C., and more preferably below about 30° C. A typical time for cure of curable compositions of the invention used for dental impressioning is within about 20 min, or preferably within about 10 min, after mixing the components of the composition. For dental duplicating applications or dental modelling applications that take place in the professional dental laboratory, cure times of up to 45 min is generally acceptable. In other applications (e.g., sealing, moulding, coating, adhesively fixing), other cure times may be typical and higher cure temperatures may be acceptable. Nevertheless, setting times in the range of about 30 min or about 1 hour can still be useful.

The material is generally regarded as cured, if the cured material fulfils the requirements for its use. For example, a dental precision impression material typically fulfils the requirements for its use when it fulfils the requirements of ISO 4823:2000 (such as compatibility with gypsum, strain in compression, recovery from deformation, detail reproduction, linear dimensional change).

Especially in the dental field two further parameters might be of some importance: working time and oral setting time.

The total working time at room temperature (23° C.) measured according to DIN EN ISO 4823:2000 for Impregum™ Garant L DuoSoft and Permadyne™ Garant L 2:1 (3M ESPE AG), both Type 3 regular setting polyether precision impression materials, is 2 min. (According to DIN EN ISO 4823: 2000 impression materials can be classified as Type 0 (kneadable), Type 1 (high viscosity), Type 2 (medium viscosity), and Type 3 (low viscosity).)

The oral setting time is given by the manufacturer in the instructions for use. According to DIN EN ISO 4823:2000 the elastomeric property recovery from deformation of the vulcanized material have to reach values of ≥96.5% within the recommended oral setting time. In addition according to DIN EN ISO 4823:2000 the elastomeric property strain in compression of the vulcanized material has to come up to a value within the range of 0.8 to 20.0% for Type 0 and Type 1 materials and in the range of 2.0 to 20.0% for Type 2 and Type 3 materials, respectively within the recommended oral setting time.

Thus, if the composition is to be used as dental impression material, appropriate working times are in a range of about 20 s to about 7 min or about 30 s to about 6 min at room temperature (23° C.). For impression materials oral setting times should be as short as possible. Suitable oral setting times are ≤about 6 min or ≤about 5 min.

According to a further embodiment, the invention is directed to the use of the a filler comprising a filler body and a filler surface, wherein the surface of the filler comprises side groups with polar moieties (as described in the text of the invention) for the production of dental compositions, especially dental impression materials and/or for increasing the tensile strength of dental compositions.

The complete disclosures of the patents, patent documents and publications cited herein are incorporated by reference in their entirety as if each were individually incorporated. Various modifications and alterations to this invention will become apparent to those skilled in the art without departing from the scope and spirit of this invention. The above specification, examples and data provide a description of the manufacture and use of the compositions and methods of the invention. The invention is not limited to the embodiments disclosed herein. One skilled in the art will appreciate that many alternative embodiments of the invention can be made without departing from the spirit and scope of thereof.

Features and advantages of this invention are further illustrated by the following examples, which are in no way intended to be limiting thereof. The particular materials and amounts thereof recited in these examples, as well as other conditions and details, should not be construed to unduly limit this invention.

EXAMPLES

Unless otherwise indicated, all parts and percentages are on a weight basis, all water is de-ionized water and all molecular weights are weight average molecular weight. Moreover, unless otherwise indicated all experiments were conducted at ambient conditions (23° C.; 1013 mbar).

Description of Measurements

Shore Hardness

Shore Hardness A is a very convenient method to obtain data about the degree of vulcanization. The value of Shore Hardness is a common number in dentistry to characterize a cured impression material.

Time dependant measurements were done according to DIN 53505. For determination of the values three independent measurements were performed. A "Handhärteprüfgerät Zwick 3150" (Zwick GmbH &Co. Ulm) was used as the measuring device.

Viscosity

The viscosity is a commonly used parameter to characterize the rheological behaviour of pasty systems.

For the measurement a rheometer with a plate/plate-system (diameter: 20 mm) was used. During the measurement which was accomplished at 23° C. a constant measuring gap was adjusted to 0.2 mm. A viscosity curve of the paste was provided by variation of the shear rate. During the measurement the shear rate was increased from 10 to 100 l/s in steps of 10 l/s. Each measuring point was kept for 5 s. Two independent measurements were performed. A "Physica Rheometer MCR300" (Anton Paar GmbH. Graz) was used as the measuring device.

Tensile Strength and Elongation at Break

Tensile strength and elongation at break were measured according to DIN 53504 form S2. The specimens were measured 24 hours after cure. For determination of the values five independent measurements were performed. A "Universalprüfmaschine Zwick 1435" (Zwick GmbH & Co. Ulm) was used as the measuring device.

Consistency Measurement

The measurement of the consistency was done according to DIN EN ISO 4823:2000.

pH Value

The pH value was determined using a mobile pH-indicator paper available from Merck KGaA. Darmstadt Germany (pH 0-14. pH indicator strips, non bleeding. Art. No. 1.09535.0001).

Particle Size

The mean particle size, if desired, can be obtained from the cumulative curve of the grain size distribution and is defined as the arithmetic average of the measured grain sizes of a certain powder mixture. Respective measurements can be done using commercially available granulometers (e.g. CILAS Laser Diffraction Particle Size Analysis Instrument).

The term d50/μm with regard to particle size measurement means that in 50% of the analyzed volume, the particles have a size below x μm. E.g., a particle size value of below 100 μm (d50/μm) means that within the analyzed volume, 50% of the particles have a size below 100 μm.

Fillers Used (Table 1)

The fillers used are commercially available (e.g. Quarzwerke Frechen, Germany; Luzenac. Graz, Austria; Hoffmann Mineral, Neuburg, Germany; Chemag, Frankfurt/Main, Germany).

TABLE 1

| Ex. | Name | pH | BET [m²/g] | Type | Silanization | CAS-No. |
|---|---|---|---|---|---|---|
| A | Silbond 600 AST | 9 | 3.0 | Quartz | Aminosilane | 014808-60-7 |
| B | Silbond 600 EST | 7 | 3.0 | Quartz | Epoxysilane | 014808-60-7 |
| C | Silbond 800 AST | 9 | 4.5 | Quartz | Aminosilane | 014808-60-7 |
| D | Silbond 800 EST | 7 | 4.5 | Quartz | Epoxysilane | 014808-60-7 |
| E | Aktisil AM | 7-9 | 8-13 | Quartz/Kaolin | 3-Aminopropyl-triethoxysilane | 014808-60-7 001318-74-7 |
| F | Celatom MW25 | 8-10 | 1.5-3.5 | Diatomaceous earth | fluxcalcinated | 68855-54-9 |
| G | Minex 10 | 9.5-10.7 | 4-5 | Nephelin-syenite | none | 060676-86-0 |
| H | Sikron SF 600 | 6-7 | 4.4 | Quartz | none | 014808-60-7 |
| I | Silbond 600 RST | 7 | 3.0 | Quartz | Trimethylsilane | 014808-60-7 |

Example 1

This example evaluates the tensile strength which can be achieved using amino- or epoxy-silanated quartz in comparison to other SiO$_2$-fillers.

The amount of filler used was 31.8% weight in the base paste in a system of base:catalyst=5:1 (by volume).

Base Pastes:

In a vessel 10.0 g tri-glyceride (trisacyclic ester of glycerine, Sasol Germany GmbH), 0.9 g imidazole compound (according to U.S. Pat. No. 4,532,268) and 9.1 g of dibenzyl toluene (Atofina, CAS 26898-17-9) were dissolved in 48.0 g difunctional aziridino polyether (from EO/THF, Mn 6000) at 90° C. Afterwards the composition was shock-cooled at 23° C. with a cooling plate. Finally 31.8 g of filler (as shown in Table 2) was added to this mixture using a laboratory kneader.

Catalyst Paste 1:

25.2 g Sulfonium salt tetrafluoroborate according to EP 1913090 B1 were mixed with 1.0 g surfactant (EO/PO copolymer; C. H. Erbslöh K G, CAS-No. 9003-11-6), and 36.3 g Acetyl Tributyl Citrate (Croda Surfactants Ltd., CAS 77-90-7) at 50° C. The solution was cooled to room temperature in a laboratory mixing machine pot. Finally, 12.5 g of Celatom MW 25 (diatomaceous earth, Solvadis Specialities GmbH, CAS 68855-54-9) and 25.0 g of highly dispersed silica, hydrophobized (HDKH, Wacker, CAS 68909-20-6) were added.

Different Base Pastes and Catalyst Paste 1 were mixed in a weight ratio Base Paste:Catalyst Paste of 1:0.24. The results regarding tensile strength, maximum elongation at break, consistency and Shore hardness A (measured 24 h after mixing) are given in Table 2. The standard deviation is given in brackets.

TABLE 2

| Ex. | Filler | ISO-consistency | Shore A (24 h) | Tensile strength | Elongation at break |
|---|---|---|---|---|---|
| 1a | Celatom MW 25 | 29 mm | 70 | 2.3 MPa (0.1) | 334% (38) |
| 1b | Minex 10 | 35 mm | 54 | 2.3 MPa (0.2) | 372% (43) |
| 1c | Sikron SF 600 | 34 mm | 57 | 2.2 MPa (0.2) | 331% (41) |
| 1d | Silbond 600 RST | 34 mm | 56 | 2.2 MPa (0.2) | 323% (46) |
| 1e | Silbond 600 AST | 34 mm | 57 | 3.2 MPa (0.2) | 325% (29) |
| 1f | Silbond 800 AST | 34 mm | 57 | 3.4 MPa (0.3) | 346% (37) |
| 1g | Silbond 800 EST | 35 mm | 55 | 3.5 MPa (0.2) | 372% (26) |

Example 2

The following pastes were prepared according to the following procedure:

Base Paste—General Procedure

In a vessel tri-glyceride, imidazole compound, N-ethyl-p-toluenesulfonamide and dibenzyl toluene were mixed with the aziridino polyether at 90° C. Afterwards the melt was shock-cooled to 23° C. with a cooling drum machine. Finally the filler according to Table 1 and the pigments/colour batch were incorporated with a kneader.

Catalyst Paste—General Procedure

The sulfonium salt tetrafluoroborate and the surfactant were mixed with acetyl tributyl citrate at 50° C. Afterwards the solution was cooled to 23° C. in a kneading machine pot. Finally diatomaceous earth, highly dispersed silica and pigments were kneaded in with a three-finger kneading machine (3M ESPE; Seefeld).

Base Paste(s) (Formulation)

TABLE 3

| Components | [g] |
|---|---|
| difunctional aziridino polyether Mn: 6000 (from EO (ethylene oxide)/ THF (tetra hydro furane) | 52.0 |
| fat (trisacyclic ester of glycerine (Sasol Germany GmbH) | 16.0 |
| dibenzyl-toluene (Atofina. CAS-No 26898-17-9) | 15.0 |
| N-ethyl-p-toluenesulfonamide (Biesterfeld. CAS-No. 80-39-7) | 2.5 |
| imidazole compound (according to U.S. Pat. No. 4,532,268) | 0.5 |
| colour batch | 2.0 |
| flavour | 0.3 |
| inorganic filler (according to Table 4 and 5) | X |

Catalyst Paste (Formulation)

19.3% sulfonium salt tetrafluoroborate (according to U.S. Pat. No. 4,167,618)

40.5% acetyl tributyl citrate (Croda Surfactants Ltd. CAS 77-90-7)

3.5% surfactant (copolymer EO/PO) (C. H. Erbsloh KG. CAS-No 9003-11-6)

12.1% diatomaceous earth (Solvadis Specialities GmbH. CAS-No 68855-54-9)

24.1% highly dispersed silica, surface treated (HDKH™, Wacker, CAS-No 68909-20-6)

0.5% pigments.

Different types and amounts of filler (as shown in Tables 4 and 5) were added to the Base Paste and the viscosity of the resulting composition evaluated with respect to different shear rates.

Result:

If a filler according to the invention was used, higher amounts of filler can be added without negatively affecting the viscosity and/or the consistency of the paste.

TABLE 4

| Ex. | Filler | [g] | Viscosity [20 1/s] | Viscosity [30 1/s] |
|---|---|---|---|---|
| 2a | Celatom MW 25 | 11.7 | 164 | 137 |
| 2b | Aktisil AM | 24.0 | 157 | 139 |

Base Paste and Catalyst Paste were mixed at 23° C. by hand spatulation. The ratio Base Paste to Catalyst Paste was 80.6 wt.-% to 19.4 wt.-% and the values for consistency, tensile strength and elongation at break evaluated. The results are given in Table 5.

TABLE 5

| Ex. | Filler | Filler [g] | Tensile strength [MPa] | Elongation at break [%] | Consistency of mixed paste [mm] |
|---|---|---|---|---|---|
| 2c | Celatom MW 25 | 11.7 | 1.72 ± 0.14 | 239 ± 36 | 35.0 |
| 2d | Aktisil AM | 24.0 | 2.57 ± 0.27 | 274 ± 37 | 35.0 |

Result:

It was found that when using the filler according to the invention, the tensile strength and elongation of break of the resulting composition can be improved, however, without negatively influencing the consistency.

The invention claimed is:

1. A hardenable dental composition comprising
    component (A) comprising a cationically hardenable compound, wherein component (A) has on average at least 2 aziridino groups or more and a molecular weight of at least about 500,
    component (B) comprising an initiator being able to initiate the hardening reaction of the cationically hardenable compound, and
    component (C) comprising a filler,
    wherein the filler comprises a filler body and a filler surface, the filler surface comprising side groups with polar moieties, the polar moieties being attached to the filler surface by a silane coupling agent being characterized by the following formula $$A_m\text{-}B\text{—}Si(R^1)_n(OR^2)_{3-n}$$

wherein
    A represents a polar moiety,
    B represents a spacer group,
    $R^1$ represents an alkyl group or an aryl group, and
    $R^2$ represents an alkyl group,
    with m=1, 2, 3 or 4 and n=0, 1 or 2;
    wherein the polar moieties are selected from thioles, phosphines, amines, amide, urethanes, thiiranes and combinations thereof; and
    wherein the hardenable dental composition is characterized by the following parameter after hardening: Tensile Strength (according to DIN 53504): at least about 3.2 MPa.

2. The dental composition according to claim 1, wherein the filler body comprises quartz, cristobalite, silicates, mixtures and combinations thereof.

3. The dental composition according to claim 1, wherein the particle size of the filler (d50 value) is within a range from about 0.1 to about 40 μm.

4. The dental composition according to claim 1, the cationically hardenable compound comprising a hardenable prepolymer, the prepolymer comprising a backbone and reactive side groups, the backbone of the prepolymer comprising moieties selected from polyether, polyesters, polyurethanes and combinations thereof.

5. The dental composition according to claim 1, the cationically hardenable compound comprising a hardenable prepolymer comprising a backbone and reactive side groups, the reactive side groups being characterized by the following formula

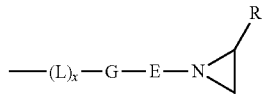

wherein
R represents H, C1-C12 alkyl, C2-C12 alkenyl, C2-C12 alkinyl, C7-C15 alkylaryl, C7-C15 arylalkyl or C3-C12 cycloalkyl, and wherein hydrogen atoms can be replaced by Cl or F and/or wherein up to about 5 carbon atoms may be replaced by atoms or group of atoms selected from O, CO, N or S,
E represents a C1-C18 branched or unbranched hydrocarbon chain wherein up to about 5 carbon atoms can be replaced by atoms or group of atoms selected from O, CO, N or S,
G represents a group selected from C(O)O, C(O)NR, C(O), C(O)C(O), C(O)(CH$_2$)$_m$C(O) with m=1 to 10, C(S)NR or CH$_2$,
L represents O, S or NR, with x=0 or 1.

6. The dental composition according to claim 1, the initiator being selected from components which can be classified as Lewis or Broensted acids, mixtures and combinations thereof.

7. The dental composition of claim 1 further comprising component (D) comprising one or more additive(s) selected from retarders, rheology modifier(s), thixotropic agent(s), diluting agent(s), inhibitor(s), pigment(s), dye(s), plastizer(s), odorous substance(s), flavouring(s), stabilizer(s), mixtures and combinations thereof.

8. The dental composition of claim 7 comprising component (E) comprising at least one surfactant.

9. The dental composition of claim 8, being characterized by at least one of the following parameters before hardening:
    Consistency (according to ISO 4823) of 0, 1, 2 or 3, or
    Setting time within about 15 min after mixing at ambient conditions.

10. The dental composition of claim 8, being characterized by at least one of the following parameters after hardening:
    Elongation at break (according to DIN 53504): at least about 150%
    Shore Hardness A (according to DIN 53504; after 24 h): at least about 20.

11. A kit of parts or container comprising a base paste and a catalyst paste separated from each other before use, wherein the base paste comprises component (A) and the catalyst paste comprises component (B), and wherein component (C) and the optional components (D) and (E) can be present either in the base paste or the catalyst paste or the base paste and the catalyst paste, and wherein components (A) to (E) are as described in claim 8.

12. The dental composition according to claim 1, wherein the polar moieties are amines.

* * * * *

UNITED STATES PATENT AND TRADEMARK OFFICE
CERTIFICATE OF CORRECTION

PATENT NO. : 8,921,475 B2
APPLICATION NO. : 13/384611
DATED : December 30, 2014
INVENTOR(S) : Joachim Zech It is certified that error appears in the above-identified patent and that said Letters Patent is hereby corrected as shown below:

Specification

Column 1

Line 63, delete "polymerzed" and insert -- polymerized --, therefor.

Column 2

Line 3, delete "compouind" and insert -- compound --, therefor.

Column 2

Line 18, delete "and or" and insert -- and/or --, therefor.

Column 3

Line 41, delete "crosslinking" and insert -- crosslinking. --, therefor.

Column 6

Line 20, delete "wettabilty" and insert -- wettability --, therefor.

Column 7

Lines 52-53, delete "l/s to 100 l/s in 10 l/s and/or 5 l/s steps." and insert
-- 1/s to 100 1/s in 10 1/s and/or 5 1/s steps). --, therefor.

Column 8

Line 31, delete "tetrahydrofurane" and insert -- tetrahydrofuran --, therefor.

Signed and Sealed this
Thirteenth Day of October, 2015

Michelle K. Lee
*Director of the United States Patent and Trademark Office*

Specification

Column 8

Line 32, delete "epichlorohydrine" and insert -- epichlorohydrin --, therefor.

Column 8

Line 46, delete "tetrahydrofurane." and insert -- tetrahydrofuran. --, therefor.

Column 10

Line 18, delete "C(O)(CH2)mC(O)" and insert -- $C(O)(CH_2)_mC(O)$ --, therefor.

Column 12

Line 35, delete "nephelinsyenite," and insert -- Nephelinesyenite, --, therefor.

Column 14

Line 45, delete "nephelinsyenit," and insert -- Nephelinesyenite, --, therefor.

Column 15

Line 20, delete "plastizer(s)," and insert -- plasticizer(s), --, therefor.

Column 15

Line 52, delete "solfonic" and insert -- sulfonic --, therefor.

Column 15

Line 53, delete "solfonic" and insert -- sulfonic --, therefor.

Column 16

Line 2, delete "solfonic" and insert -- sulfonic --, therefor.

Column 17

Lines 12-13 (approx.), delete "surfactancts" and insert -- surfactants --, therefor.

Column 18

Line 2, delete "—SiR'2—" and insert -- —SiR"2— --, therefor.

Specification

Column 23

Line 8, delete "the a" and insert -- the --, therefor.

Column 24,

Lines 12-13 (approx.), delete "l/s in steps of 10 l/s." and insert -- 1/s in steps of 10 1/s. --, therefor.

Claims

Column 27

Line 50, in Claim 5, delete "claim 1," and insert -- claim 4, --, therefor.

Column 28

Lines 28-29, in Claim 7, delete "plastizer(s)," and insert -- plasticizer(s), --, therefor.